(12) United States Patent
Yoshida et al.

(10) Patent No.: US 12,036,069 B2
(45) Date of Patent: Jul. 16, 2024

(54) ULTRASONIC DIAGNOSIS SYSTEM

(71) Applicant: FUJI CORPORATION, Chiryu (JP)

(72) Inventors: Naofumi Yoshida, Obu (JP); Takeshi Sato, Nagoya (JP); Yasuhiro Yamashita, Toyoake (JP)

(73) Assignee: FUJI CORPORATION, Chiryu (JP)

( * ) Notice: Subject to any disclaimer, the term of this patent is extended or adjusted under 35 U.S.C. 154(b) by 81 days.

(21) Appl. No.: 17/777,354

(22) PCT Filed: Dec. 5, 2019

(86) PCT No.: PCT/JP2019/047622
§ 371 (c)(1),
(2) Date: May 17, 2022

(87) PCT Pub. No.: WO2021/111581
PCT Pub. Date: Jun. 10, 2021

(65) Prior Publication Data
US 2022/0401067 A1    Dec. 22, 2022

(51) Int. Cl.
*A61B 8/00* (2006.01)
*A61B 8/08* (2006.01)
(52) U.S. Cl.
CPC .......... *A61B 8/4254* (2013.01); *A61B 8/0891* (2013.01)
(58) Field of Classification Search
CPC ... A61B 8/4254; A61B 8/0891; A61B 8/4218; A61B 8/4245; A61B 8/4263; A61B 8/429; A61B 8/54; A61B 6/465
See application file for complete search history.

(56) References Cited

U.S. PATENT DOCUMENTS

| 2018/0000511 | A1 | 1/2018 | Fujie et al. | |
| 2018/0338745 | A1* | 11/2018 | Takeuchi | A61B 90/06 |
| 2021/0322106 | A1* | 10/2021 | Mo | A61B 5/489 |

FOREIGN PATENT DOCUMENTS

| CN | 108814691 A | * 11/2018 | ......... A61B 17/3403 |
| CN | 108814691 A | 11/2018 | |
| CN | 110488745 A | * 11/2019 | |
| EP | 3 574 841 A1 | 12/2019 | |
| JP | 2006-238913 A | 9/2006 | |
| JP | 2011-104191 A | 6/2011 | |
| JP | 6611104 B1 | 11/2019 | |
| WO | WO 2016/111255 A1 | 7/2016 | |

OTHER PUBLICATIONS

International Search Report issued Jan. 28, 2020 in PCT/JP2019/047622 filed on Dec. 5, 2019, 2 pages.

* cited by examiner

*Primary Examiner* — Joel Lamprecht
(74) *Attorney, Agent, or Firm* — Oblon, McClelland, Maier & Neustadt, L.L.P.

(57) ABSTRACT

An ultrasonic diagnosis system includes a reaction force detection sensor that detects a reaction force acting on an ultrasonic probe when the ultrasonic probe is pressed against a body surface of a subject. Then, the ultrasonic diagnosis system estimates the push-in amount of the ultrasonic probe with respect to the subject by using the reaction force detection sensor during the ultrasonic diagnosis to output a display or a warning of the estimated push-in amount of the ultrasonic probe to the output device.

3 Claims, 6 Drawing Sheets

ULTRASONIC DIAGNOSIS SYSTEM

TECHNICAL FIELD

The present specification discloses an ultrasonic diagnosis system.

BACKGROUND ART

Conventionally, an ultrasonic diagnosis system including an ultrasonic diagnosis device having an ultrasonic probe, a robot for the ultrasonic diagnosis device for operating the ultrasonic probe, and a control device for controlling the robot for the ultrasonic diagnosis device has been proposed (see Patent Literature 1, for example). The ultrasonic diagnosis device has a probe state detecting function for detecting disposition information of the ultrasonic probe with respect to a blood vessel when an ultrasonic image is acquired by image processing based on the ultrasonic image. The control device controls the robot for the ultrasonic diagnosis device so as to dispose the ultrasonic probe in an optimal state at the time of data measurement by the ultrasonic diagnosis device based on the disposition state of the ultrasonic probe detected by the ultrasonic diagnosis device.

PATENT LITERATURE

Patent Literature 1: JP-A-2011-104191

BRIEF SUMMARY

Technical Problem

In an ultrasonic diagnosis device, the higher the frequency of an ultrasonic wave radiated from an ultrasonic probe, the higher the resolution, but in the case of inspecting the inside of the body of a subject, the higher the frequency of the ultrasonic wave, the shallower the depth at which the ultrasonic wave reaches. In the case of inspecting a blood vessel in the body of the subject by using an ultrasonic diagnosis device, the distance from the skin to the blood vessel varies depending on the body size of the subject, and in general, a subject with a larger body size has a longer distance than a subject with a smaller body size. That is, in a case where a blood vessel of a subject having a large body size is inspected, the ultrasonic wave radiated from the ultrasonic probe hardly reaches the blood vessel. Therefore, when inspecting the blood vessel of a subject having a large body size, in some cases, the ultrasonic probe may be excessively strongly pressed on the skin of the subject, causing the subject to feel pain or discomfort.

It is a main object of the present disclosure to provide an ultrasonic diagnosis system capable of making a push-in amount of an ultrasonic probe with respect to a subject appropriate during ultrasonic diagnosis regardless of the body size of the subject.

Solution to Problem

The present disclosure employs the following means in order to achieve the above-described main object.

An ultrasonic diagnosis system according to the present disclosure includes an ultrasonic diagnosis device having an ultrasonic probe, a reaction force detection sensor configured to detect a reaction force acting on the ultrasonic probe when the ultrasonic probe is pressed against a body surface of a subject, a control device configured to estimate a push-in amount of the ultrasonic probe with respect to the subject by using the reaction force detection sensor, and an output device configured to output a display or a warning of the push-in amount of the ultrasonic probe.

The ultrasonic diagnosis system of the present disclosure includes a reaction force detection sensor configured to detect a reaction force acting on an ultrasonic probe when the ultrasonic probe is pressed against a body surface of a subject. Then, the ultrasonic diagnosis system estimates the push-in amount of the ultrasonic probe with respect to the subject by using the reaction force detection sensor during the ultrasonic diagnosis to output a display or a warning of the estimated push-in amount of the ultrasonic probe to the output device. As a result, since the ultrasonic probe can be pressed against the subject while confirming how much the ultrasonic probe is currently pushed, it is possible to make the push-in amount of the ultrasonic probe with respect to the subject appropriate regardless of the body size of the subject.

DESCRIPTION OF EMBODIMENTS

Figure 1:
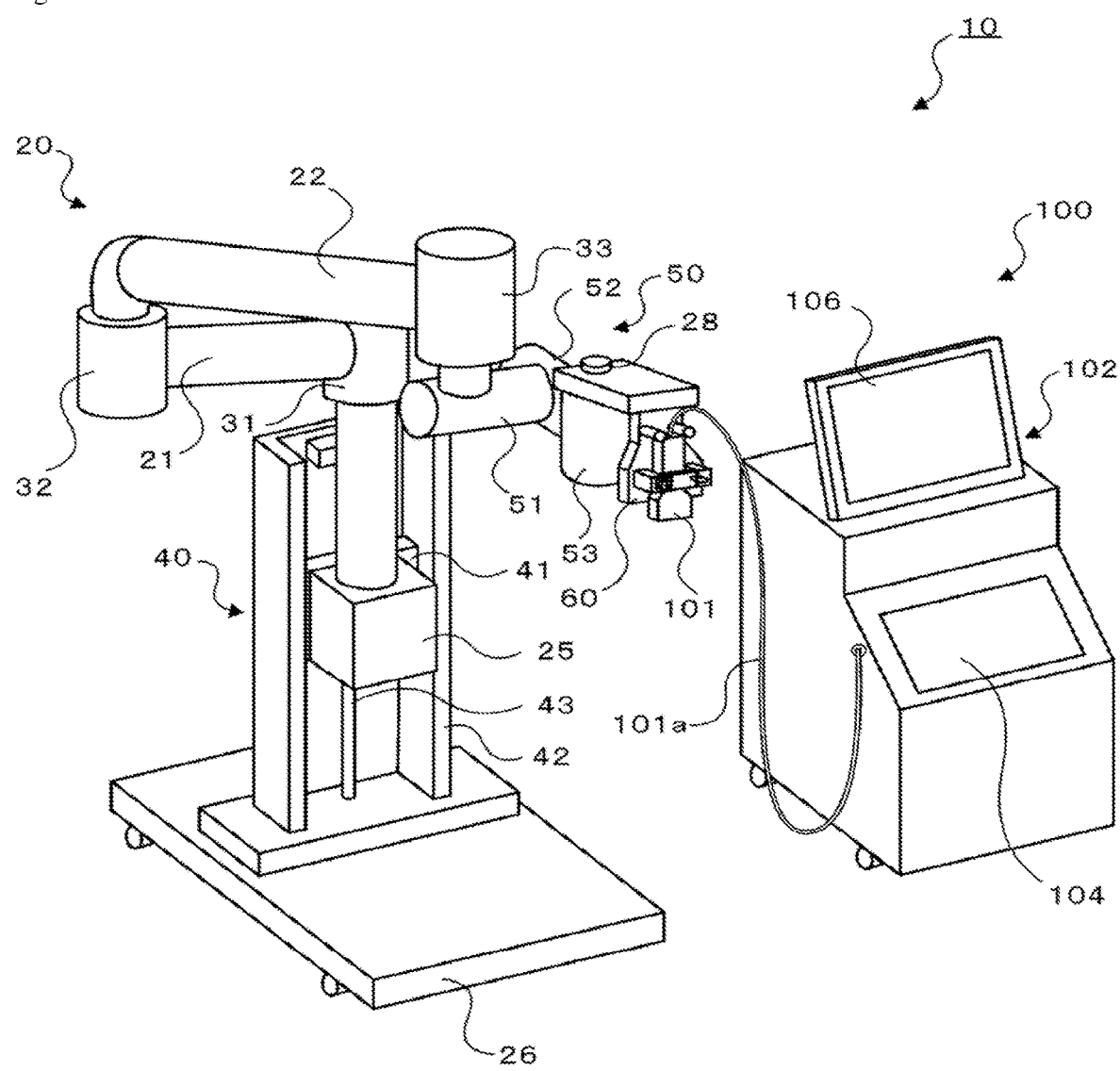
FIG. 1 is an appearance perspective view of ultrasonic diagnosis system 10.
Figure 2:
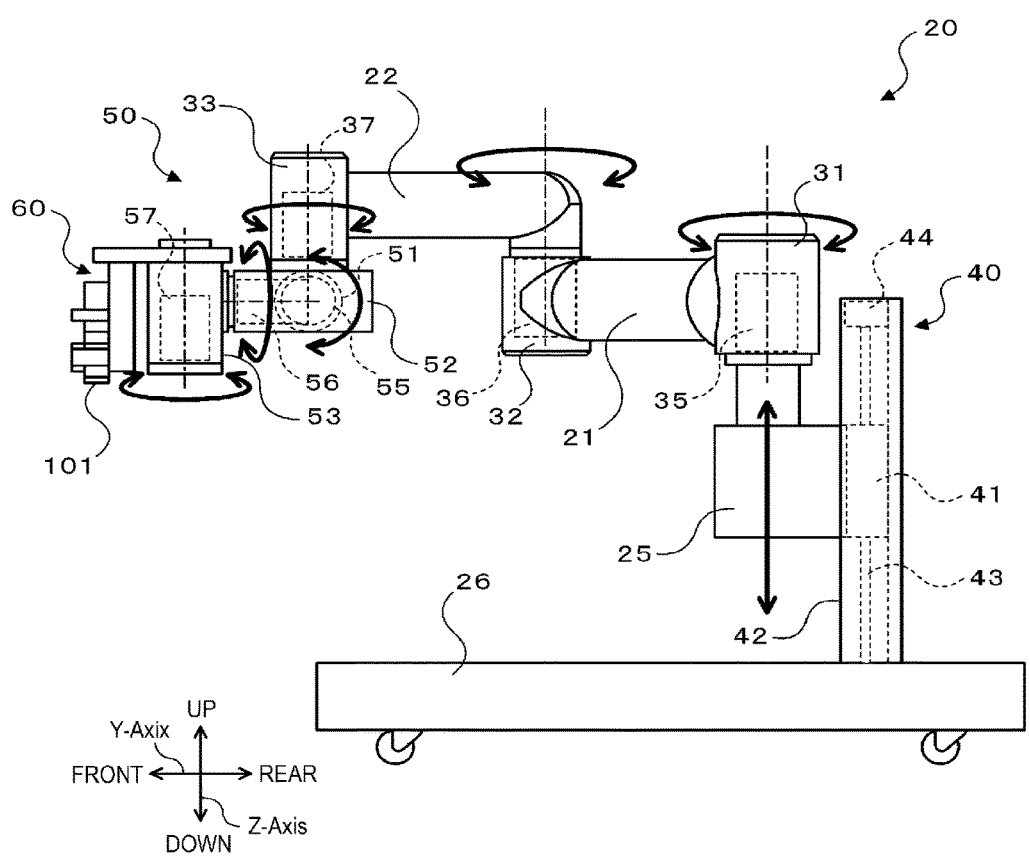
FIG. 2 is a side view of robot 20.
Figure 3:
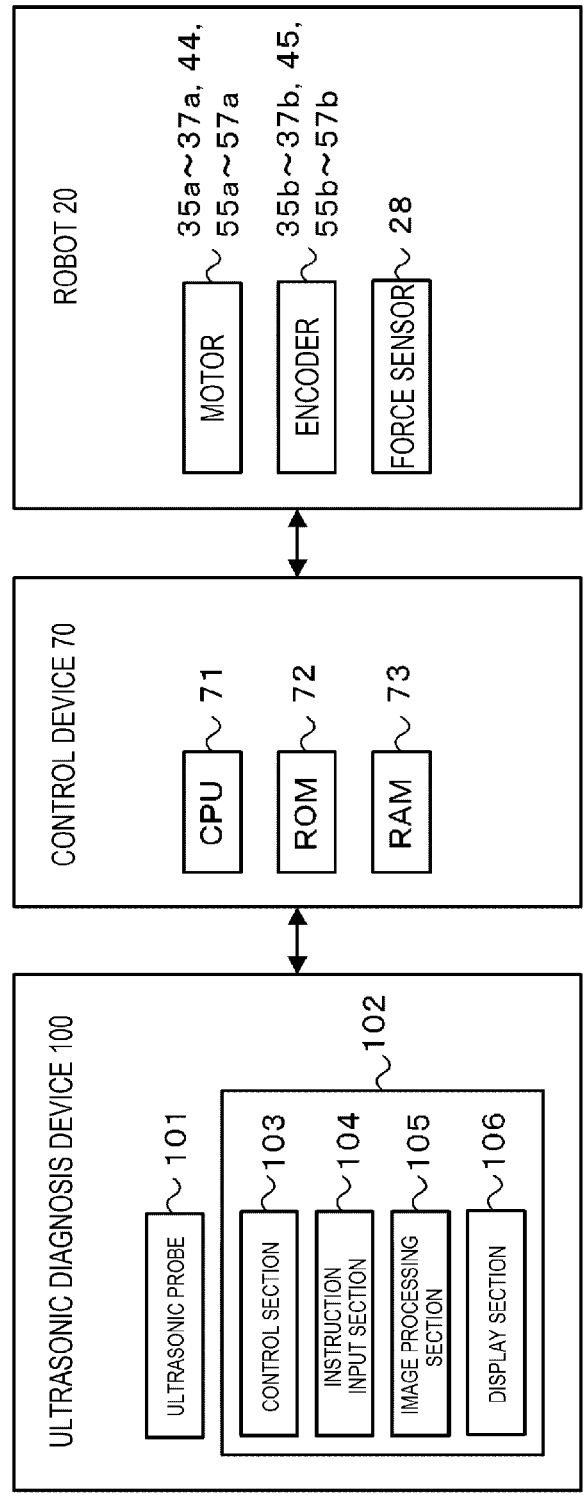
FIG. 3 is a block view illustrating an electrical connection relationship among robot 20, control device 70, and ultrasonic diagnosis device 100.

Next, an embodiment of the present disclosure will be described with reference to drawings. FIG. 1 is an appearance perspective view of ultrasonic diagnosis system 10. FIG. 2 is a side view of robot 20. FIG. 3 is a block view illustrating an electrical connection relationship among robot 20, control device 70, and ultrasonic diagnosis device 100. In FIG. 1, a left-right direction is an X axis direction, a front-rear direction is a Y-axis direction, and an up-down direction is a Z-axis direction.

Ultrasonic diagnosis system 10 performs ultrasonic diagnosis by holding ultrasonic probe 101 in robot 20, and driving robot 20 such that ultrasonic probe 101 is pressed against the skin of a subject. In the present embodiment, ultrasonic diagnosis system 10 is used for a carotid artery echo inspection in which an ultrasonic wave is applied to a carotid artery of the subject, a cross-sectional image in a short axis direction and a cross-sectional image in a long axis direction of the carotid artery are acquired, and a state of a blood vessel is checked from the acquired images. As illustrated in FIGS. 1 and 2, ultrasonic diagnosis system 10 includes robot 20, force sensor 28 (see FIG. 3), control device 70 (see FIG. 3) for controlling robot 20, and ultrasonic diagnosis device 100.

Ultrasonic diagnosis device 100 includes ultrasonic probe 101 and ultrasonic diagnosis device main body 102 to which ultrasonic probe 101 is connected via cable 101a. Ultrasonic diagnosis device main body 102 includes control section 103 configured to control the entire device, instruction input section 104 configured to input an instruction to initiate diagnosis or the like, image processing section 105 configured to process a received signal from ultrasonic probe 101 to generate an ultrasonic image, and display section 106 configured to display the generated ultrasonic image.

Robot 20 includes first arm 21, second arm 22, base 25, base plate 26, first arm driving device 35, second arm driving device 36, orientation holding device 37, lifting and lowering device 40, three-axis rotation mechanism 50, and holder 60. First arm 21, second arm 22, and three-axis rotation mechanism 50 may be simply referred to as an arm.

The base end section of first arm 21 is coupled to base 25 via first joint shaft 31 extending in the up-down direction (Z-axis direction). First arm driving device 35 includes motor 35*a* and encoder 35*b*. The rotation shaft of motor 35*a* is connected to first joint shaft 31 via a deceleration device (not illustrated). First arm driving device 35 causes first arm 21 to turn (pivot) along a horizontal plane (XY-plane) around first joint shaft 31 as a fulcrum by rotationally driving first joint shaft 31 by motor 35*a*. Encoder 35*b* is attached to the rotation shaft of motor 35*a*, and is configured as a rotation encoder that detects a rotational displacement amount of motor 35*a*.

The base end section of second arm 22 is coupled to the tip end portion of first arm 21 via second joint shaft 32 extending in the up-down direction. Second arm driving device 36 includes motor 36*a* and encoder 36*b*. The rotation shaft of motor 36*a* is connected to second joint shaft 32 via a deceleration device (not illustrated). Second arm driving device 36 causes second arm 22 turn (pivot) along a horizontal plane around second joint shaft 32 as a fulcrum by rotationally driving second joint shaft 32 by motor 36*a*. Encoder 36*b* is attached to the rotation shaft of motor 36*a*, and is configured as a rotation encoder that detects the rotational displacement amount of motor 36*a*.

Base 25 is provided so as to be lifted and lowered with respect to base plate 26 by lifting and lowering device 40 installed on base plate 26. As illustrated in FIGS. 1 and 2, lifting and lowering device 40 includes slider 41 fixed to the base 25, guide member 42 fixed to base plate 26 and extending in the up-down direction to guide the movement of slider 41, ball screw shaft 43 (lifting and lowering shaft) extending in the up-down direction and screwed with a ball screw nut (not illustrated) fixed to slider 41, motor 44 rotationally driving ball screw shaft 43, and encoder 45 (see FIG. 3). Lifting and lowering device 40 causes base 25 fixed to slider 41 to move in the up-down direction along with guide member 42 by rotationally driving ball screw shaft 43 by motor 44. The encoder 45 is configured as a linear encoder that detects a position in the up-down direction (a lifting and lowering position) of slider 41 (base 25).

Three-axis rotation mechanism 50 is coupled to the tip end portion of second arm 22 via orientation holding shaft 33 extending in the up-down direction. Three-axis rotation mechanism 50 includes first rotation shaft 51, second rotation shaft 52, and third rotation shaft 53 that are orthogonal to each other, first rotation device 55 that rotates first rotation shaft 51, second rotation device 56 that rotates second rotation shaft 52, and third rotation device 57 that rotates third rotation shaft 53. First rotation shaft 51 is supported in an orientation orthogonal to orientation holding shaft 33. Second rotation shaft 52 is supported in an orientation orthogonal to first rotation shaft 51. Third rotation shaft 53 is supported in an orientation orthogonal to second rotation shaft 52. First rotation device 55 includes motor 55*a* for rotationally driving first rotation shaft 51, and encoder 55*b* attached to the rotation shaft of motor 55*a* to detect the rotational displacement amount of motor 55*a*. Second rotation device 56 includes motor 56*a* for rotationally driving second rotation shaft 52, and encoder 56*b* attached to the rotation shaft of motor 56*a* to detect the rotational displacement amount of motor 56*a*. Third rotation device 57 includes motor 57*a* for rotationally driving third rotation shaft 53, and encoder 57*b* attached to the rotation shaft of motor 57*a* to detect the rotational displacement amount of motor 57*a*. Holder 60 is attached to third rotation shaft 53. In the present embodiment, holder 60 is fixed at a position spaced apart from third rotation shaft 53 in the radial direction. Ultrasonic probe 101 held by holder 60 moves with an arcuate trajectory about third rotation shaft 53 by the rotation of third rotation shaft 53. Holder 60 may be attached such that ultrasonic probe 101 is positioned coaxially with third rotation shaft 53.

Robot 20 of the present embodiment can move ultrasonic probe 101 to any position in any orientation by a combination of the translational movement in three directions of the X-axis direction, the Y-axis direction, and the Z-axis direction by first arm driving device 35, second arm driving device 36, and lifting and lowering device 40, and the rotational movement in three directions of the X axis (pitching), the Y axis (rolling), and the Z axis (yawing) by three-axis rotation mechanism 50.

Orientation holding device 37 holds the orientation of three-axis rotation mechanism 50 (the direction of first rotation shaft 51) in a fixed direction regardless of the orientations of first arm 21 and second arm 22. Orientation holding device 37 includes motor 37*a* and encoder 37*b*. The rotation shaft of motor 37*a* is connected to orientation holding shaft 33 via a deceleration device (not illustrated). Orientation holding device 37 sets a target rotation angle of orientation holding shaft 33 based on the rotation angle of first joint shaft 31 and the rotation angle of second joint shaft 32 such that the axial direction of first rotation shaft 51 is always in the left-right direction (the X-axis direction), and drives to control motor 37*a* so that orientation holding shaft 33 is at the target rotation angle. As a result, the control of the translational movement in the three directions and the control of the rotational movement in the three directions can be independently performed to facilitate the control.

Force sensor 28 is attached to the tip end of the arm, and detects a force component acting in each axial direction of the X axis, the Y axis, and the Z axis as an external force acting on the arms, and a torque component acting around each axis.

As illustrated in FIG. 3, control device 70 is configured as a microprocessor centered on CPU 71, and includes ROM 72, RAM 73, an input/output port, and a communication port (not illustrated) in addition to CPU 71. The detection signal from force sensor 28, detection signals from respective encoders 35*b*, 36*b*, 37*b*, 45, 55*b*, 56*b*, 57*b*, and the like are input to control device 70 via input ports. In addition, a drive signal to each of motors 35*a*, 36*a*, 37*a*, 44, 55*a*, 56*a*, and 57*a* is output from control device 70 via output ports. Control device 70 communicates with control section 103 of ultrasonic diagnosis device 100 via a communication port to exchange data.

Figure 4:
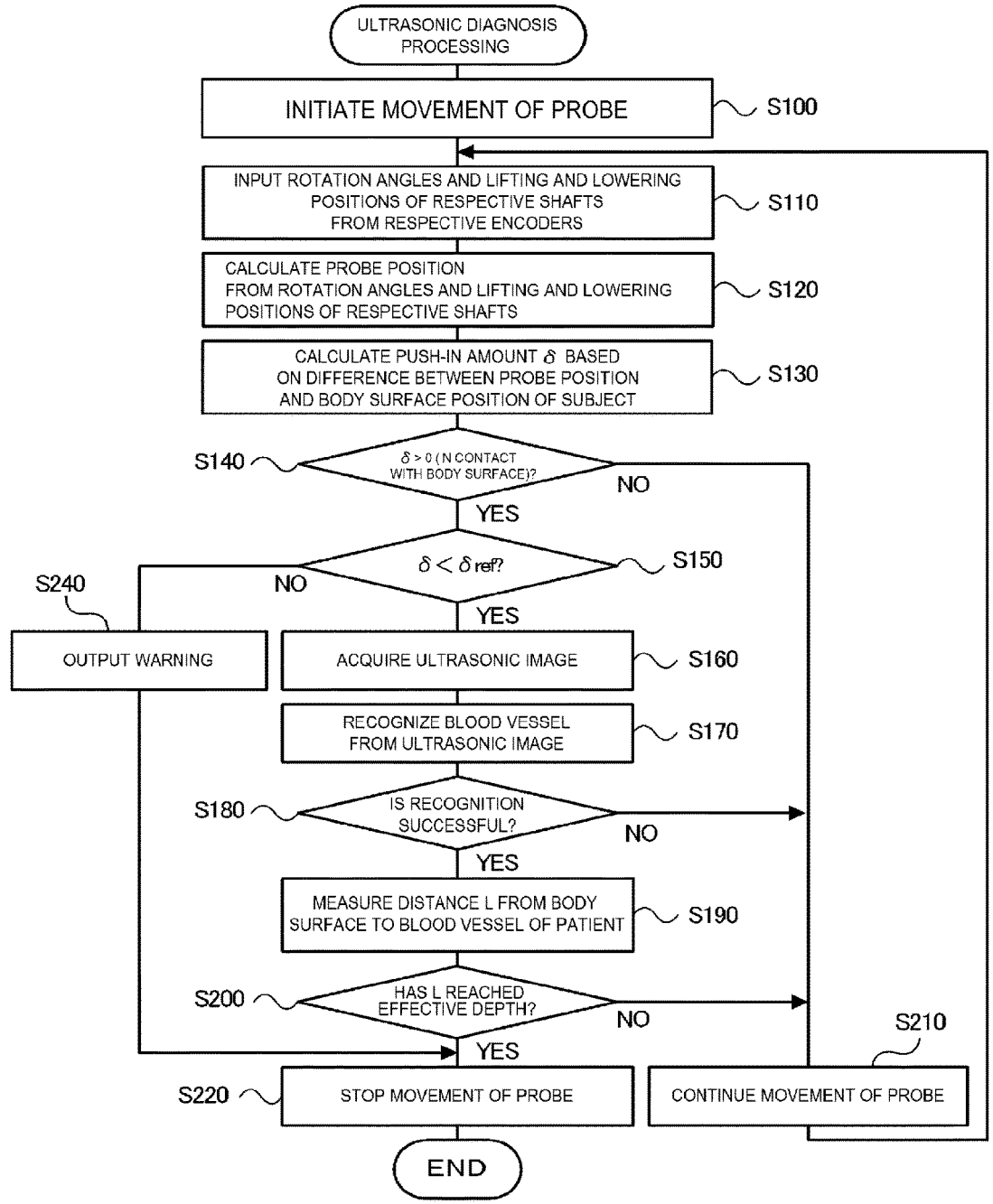
FIG. 4 is a flowchart illustrating an example of ultrasonic diagnosis processing.

Next, an operation of ultrasonic diagnosis system 10 according to the present embodiment configured as described above will be described. FIG. 4 is a flowchart illustrating an example of ultrasonic diagnosis processing executed by CPU 71 of control device 70.

When ultrasonic diagnosis processing is executed, CPU 71 first drives to control the corresponding motor of robot 20 to initiate the movement of ultrasonic probe 101 toward a subject (step S100). Ultrasonic probe 101 is performed in the following manner. That is, CPU 71 determines a target position and a target orientation of an arm holding ultrasonic probe 101 according to a task program created in advance. Subsequently, CPU 71 sets a target rotation angle of first joint shaft 31, a target rotation angle of second joint shaft 32, a target rotation angle of orientation holding shaft 33, a target lifting and lowering position of base 25, a target rotation angle of first rotation shaft 51, a target rotation angle of second rotation shaft 52, and a target rotation angle of third rotation shaft 53, respectively, for moving the arm to a target position in a target orientation. Then, CPU 71 controls the corresponding motor so that the rotation angle or the lifting and lowering position detected by respective encoders 35b, 36b, 37b, 45, 55b, 56b, and 57b coincides with the corresponding target rotation angle or target lifting and lowering position.

Figure 5:
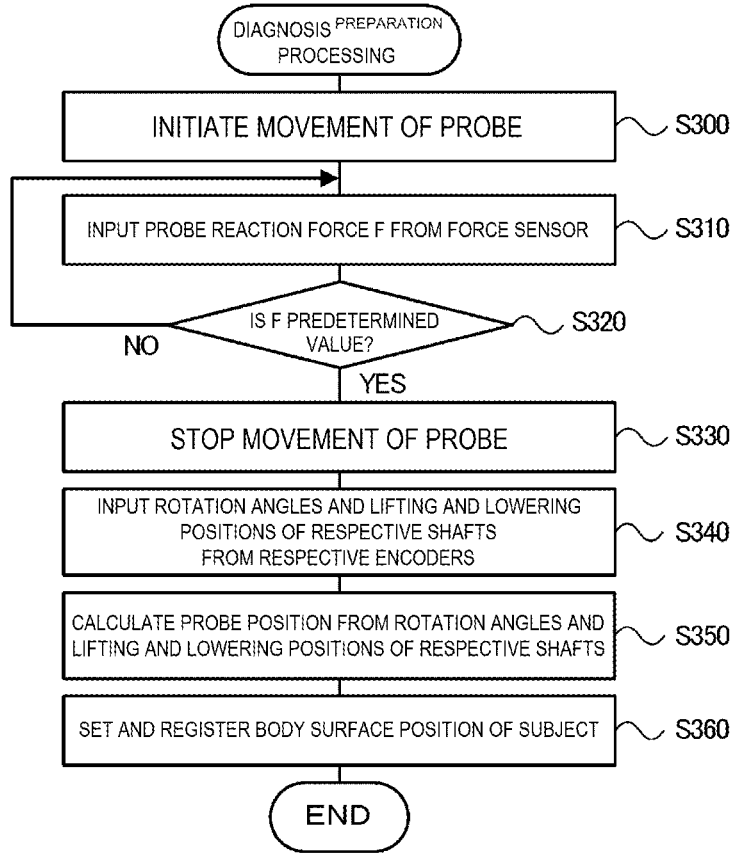
FIG. 5 is a flowchart illustrating an example of diagnosis preparation processing.

When initiating the movement of ultrasonic probe 101, CPU 71 inputs the rotation angles and the lifting and lowering positions of the respective shafts (first joint shaft 31, second joint shaft 32, first to third rotation shafts 51 to 53, and the lifting and lowering shaft) detected by respective encoders 35b, 36b, 37b, 45, 55b, 56b, and 57b (step S110). Subsequently, CPU 71 calculates the tip end position (probe position) of ultrasonic probe 101 by the forward kinematics based on the input rotation angles and the lifting and lowering positions of the respective shafts (step S120). In step S130, CPU 71 calculates push-in amount $\delta$ of ultrasonic probe 101 with respect to the subject based on the difference between the calculated probe position and the body surface position of the subject. Here, the body surface position of the subject is used as measured by the diagnosis preparation processing of FIG. 5 performed prior to the ultrasonic diagnosis processing.

In the diagnosis preparation processing, CPU 71 first initiates the movement of ultrasonic probe 101 toward the subject (step S300). Subsequently, CPU 71 inputs reaction force F applied to ultrasonic probe 101 from the body surface when ultrasonic probe 101 contacts the body surface of the subject from force sensor 28 (step S310), and waits until the input reaction force F reaches a predetermined value slightly larger than a value 0 (step S320). The processing in step S320 is to determine whether ultrasonic probe 101 is in a state of contact with the subject without being hardly pushed in. When it is determined that reaction force F has reached the predetermined value, CPU 71 stops the movement of ultrasonic probe 101 (step S330), inputs the rotation angles and the lifting and lowering positions of the respective shafts detected by respective encoders 35b, 36b, 37b, 45, 55b, 56b, and 57b (step S340), and calculates the probe position based on the rotation angles and the lifting and lowering positions of the respective shafts that have been input (step S350). Then, CPU 71 sets the calculated probe position as the body surface position of the subject, registers the set body surface position in RAM 73 (step S360), and ends the diagnosis preparation processing.

Returning to the ultrasonic diagnosis processing, CPU 71 determines whether the calculated push-in amount $\delta$ is larger than the value 0 (step S140). This processing is to determine whether ultrasonic probe 101 is in contact with the body surface of the subject. When it is determined that push-in amount $\delta$ is not larger than the value 0, CPU 71 continues the movement of ultrasonic probe 101 (step S210), returns to step S110, and repeats the processing. On the other hand, when it is determined that push-in amount $\delta$ is larger than the value 0, CPU 71 further determines whether push-in amount $\delta$ is less than threshold value $\delta$ref (step S150). Threshold value $\delta$ref is a threshold value for determining whether the pushing of ultrasonic probe 101 with respect to the body surface of the subject is excessive. Therefore, in a case where push-in amount $\delta$ is less than threshold value $\delta$ref, it is determined that push-in amount $\delta$ is within the allowable range and an excessive load is not generated on the subject.

Figure 6:
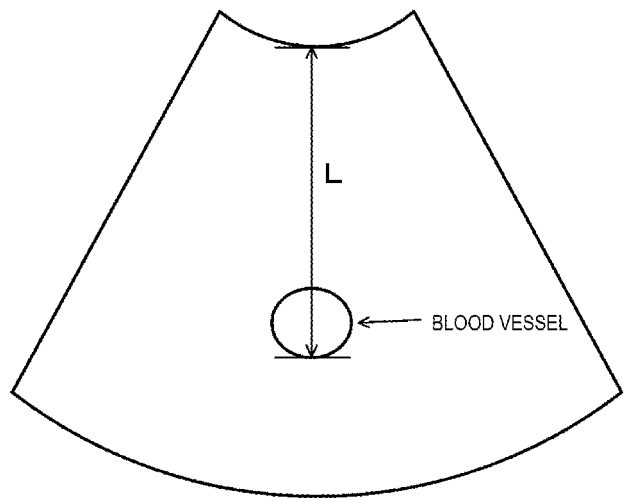
FIG. 6 is an explanatory view illustrating distance L.

In step S160, when it is determined that push-in amount $\delta$ is less than threshold value $\delta$ref, CPU 71 acquires the ultrasonic image generated by image processing section 105 of ultrasonic diagnosis device 100. Subsequently, CPU 71 performs image processing of recognizing a blood vessel from the acquired ultrasonic image (step S170) to determine whether the recognition is successful (step S180). This processing can be performed, for example, by applying pattern matching to the acquired ultrasonic image. When it is determined that the recognition is not successful, CPU 71 continues the movement of ultrasonic probe 101 (step S210), returns to step S110, and repeats the processing. On the other hand, when it is determined that the recognition is successful, CPU 71 measures distance L from the body surface to the blood vessel of the subject (step S190). FIG. 6 is an explanatory view for explaining distance L. In the drawing, the upper end represents a body surface, and the up-down direction represents a depth in the body. Distance L can be measured by the distance from the upper end of the ultrasonic image to the blood vessel.

After measuring distance L, CPU 71 determines whether the measured distance L has reached the effective depth of ultrasonic waves in a living body (step S200). The effective depth is determined in advance according to the specifications of ultrasonic probe 101 such as the frequency of the ultrasonic wave to be radiated. When it is determined that distance L has not reached the effective depth of ultrasonic waves, CPU 71 continues the movement of the ultrasonic probe 101 (step S210), returns to step S110, and repeats the processing. On the other hand, when it is determined that distance L has reached the effective depth of ultrasonic waves, CPU 71 stops the movement of ultrasonic probe 101 (step S220), and ends the ultrasonic diagnosis processing. As described above, in the present embodiment, CPU 71 gradually increases the push-in amount of ultrasonic probe 101 with respect to the subject until distance L reaches the effective depth of ultrasonic waves, and stops the pushing of ultrasonic probe 101 when distance L reaches the effective depth. As a result, the push-in amount of ultrasonic probe 101 with respect to the subject can be set to a minimum push-in amount that falls within the effective depth of ultrasonic waves, that is, a minimum push-in amount that can secure the resolution of the image for normally executing the ultrasonic diagnosis. As a result, it is possible to further reduce the load on the subject during the ultrasonic diagnosis.

Figure 7:
FIG. 7 is an explanatory view illustrating an example of a warning screen.

When it is determined in step S150 that push-in amount $\delta$ is equal to or larger than threshold value $\delta$ref, CPU 71 outputs a warning (step S240), stops the movement of ultrasonic probe 101 (step S220), and ends the ultrasonic diagnosis processing. Processing in step S240 is performed by transmitting a warning signal to control section 103 of ultrasonic diagnosis device 100, so that control section 103 receiving the warning signal displays a warning screen on display section 106. FIG. 7 is an explanatory view illustrating an example of a warning screen. As illustrated in the drawing, the warning screen includes a warning message for calling the attention of a diagnostician and the current push-in amount of ultrasonic probe 101. As a result, it is possible to notify the diagnostician that the ultrasonic probe 101 may be pushed into the subject by an excessive force.

Any one of the warning message and the current push-in amount may be displayed on the warning screen. In addition, CPU 71 may output a warning sound in step S240.

Here, a correspondence relationship between elements of the embodiment and elements of the present disclosure s will be described. That is, ultrasonic probe 101 of the present embodiment corresponds to the ultrasonic probe, ultrasonic diagnosis device 100 corresponds to the ultrasonic diagnosis device, force sensor 28 corresponds to the reaction force detection sensor, control device 70 corresponds to the control device, and display section 106 of ultrasonic diagnosis device 100 corresponds to the output device of the present disclosure. In addition, robot 20 corresponds to a moving device. Encoders 35b, 36b, 37b, 45, 55b, 56b, and 57b correspond to position sensors.

Needless to say, the present disclosure is not limited to the embodiment that has been described heretofore in any way and may be implemented in various forms without departing from the technical scope of the present disclosure.

For example, in the above-described embodiment, control device 70 sets, as the body surface position of the subject, the probe position when ultrasonic probe 101 is caused to contact the body surface of the subject so that reaction force F applied to ultrasonic probe 101 detected by force sensor 28 reaches a predetermined value slightly larger than the value 0. However, by capturing an image of the subject with the camera and calculating the distance to the body surface of the subject based on the captured image, control device 70 may set the body surface position of the subject based on the calculated distance.

In the above embodiment, control device 70 calculates push-in amount δ by the difference between the position of ultrasonic probe 101 (probe position) pressed against the subject during the ultrasonic diagnosis and the position of the body surface of the subject. However, control device 70 may calculate push-in amount δ based on the magnitude of the reaction force F applied to ultrasonic probe 101 detected by force sensor 28. In this case, push-in amount δ may be calculated so as to be larger as reaction force F is larger.

In the above embodiment, robot 20 is configured as a seven-axis articulated robot capable of translational movement in three directions and rotational movement in three directions. However, the number of axes may be any number. Robot 20 may be configured by a so-called vertical articulated robot, a horizontal articulated robot, or the like.

In the above-described embodiment, ultrasonic diagnosis system 10 includes robot 20 that automatically operates in accordance with a task program. However, the ultrasonic diagnosis system may include a master device that is installed at a remote location and can be operated by an operator (diagnostician), and a remote control robot that is connected to the master device via a communication line, holds an ultrasonic probe on the arm, and operates the arm in response to the operation of the master device. In this case, the control device of the remote control robot may transmit a warning signal to the master device in order to give a warning (output of a warning sound or a warning display) to the operator from the master device side when the push-in amount δ of the ultrasonic probe on the subject is equal to or larger than threshold value δref.

As described above, an ultrasonic diagnosis system of the present disclosure includes an ultrasonic diagnosis device having an ultrasonic probe, a reaction force detection sensor that detects a reaction force acting on the ultrasonic probe when the ultrasonic probe is pressed against a body surface of a subject, a control device that estimates a push-in amount of the ultrasonic probe with respect to the subject by using the reaction force detection sensor, and an output device that outputs a display or a warning of the push-in amount of the ultrasonic probe.

The ultrasonic diagnosis system of the present disclosure includes a reaction force detection sensor configured to detect a reaction force acting on an ultrasonic probe when the ultrasonic probe is pressed against a body surface of a subject. Then, the ultrasonic diagnosis system estimates the push-in amount of the ultrasonic probe with respect to the subject by using the reaction force detection sensor during the ultrasonic diagnosis to output a display or a warning of the estimated push-in amount of the ultrasonic probe to the output device. As a result, since the ultrasonic probe can be pressed against the subject while confirming how much the ultrasonic probe is currently pushed, it is possible to make the push-in amount of the ultrasonic probe with respect to the subject appropriate regardless of the body size of the subject.

The ultrasonic diagnosis system of the present disclosure may further include a moving device that moves the ultrasonic probe, in which the control device recognizes a blood vessel in a body of the subject based on an ultrasonic image obtained from the ultrasonic diagnosis device during ultrasonic diagnosis, measures a distance from the ultrasonic probe to the blood vessel, and controls the moving device so that the ultrasonic probe is pushed into the subject with a minimum push-in amount by which the distance falls within an effective depth of ultrasonic waves in the body. Accordingly, it is possible to minimize the load on the subject during the ultrasonic diagnosis. In this case, the ultrasonic diagnosis system may further include a position sensor that detects a position of the ultrasonic probe, in which the control device estimates the push-in amount of the ultrasonic probe based on a position of the ultrasonic probe detected by the position sensor when the moving device is controlled so that the ultrasonic probe contacts the body surface of the subject in a state in which a reaction force detected by the reaction force detection sensor is a predetermined value prior to ultrasonic diagnosis, and a position of the ultrasonic probe detected by the position sensor when the moving device is controlled so that the ultrasonic probe is pressed against the body surface of the subject during ultrasonic diagnosis. In this way, it is possible to more accurately estimate the push-in amount of the ultrasonic probe. The moving device may be an articulated robot.

The ultrasonic diagnosis system may have the following configuration. That is, a second ultrasonic diagnosis system of the present disclosure includes an ultrasonic diagnosis device having an ultrasonic probe, a moving device that moves the ultrasonic probe, and a control device that recognizes a blood vessel in a body of the subject based on an ultrasonic image obtained from the ultrasonic diagnosis device during ultrasonic diagnosis, measures a distance from the ultrasonic probe to the blood vessel, and controls the moving device so that the ultrasonic probe is pushed into the subject with a minimum push-in amount by which the distance falls within an effective depth of ultrasonic waves in the body.

INDUSTRIAL APPLICABILITY

The present disclosure can be applied to, for example, the manufacturing industry of a device for measuring the positional deviation amount of an ultrasonic probe.

REFERENCE SIGNS LIST

10 ultrasonic diagnosis system
20 robot 21 first arm
22 second arm
25 base
26 base plate
28 force sensor
31 first joint shaft
32 second joint shaft
33 orientation holding shaft
35 first arm driving device
35a motor
35b encoder
36 second arm driving device
36a motor
36b encoder
37 orientation holding device
37a motor
37b encoder
40 lifting and lowering device
41 slider
42 guide member
43 ball screw shaft
44 motor
45 encoder
50 three-axis rotation mechanism
51 first rotation shaft
52 second rotation shaft
53 third rotation shaft
55 first rotation device
55a motor
55b encoder
56 second rotation device
56a motor
56b encoder
57 third rotation device
57a motor
57b encoder
60 holder
100 ultrasonic diagnosis device
101 ultrasonic probe
101a cable
102 ultrasonic diagnosis device main body
103 control section
104 instruction input section
105 image processing section
106 display section

The invention claimed is:

1. An ultrasonic diagnosis system comprising:
an ultrasonic diagnosis device having an ultrasonic probe;
an articulated robot configured to move the ultrasonic probe;
a position sensor configured to detect a position of the ultrasonic probe;
a reaction force detection sensor configured to detect a reaction force acting on the ultrasonic probe when the ultrasonic probe is pressed against a body surface of a subject;
a control device configured to perform an ultrasonic diagnosis by
performing a diagnosis preparation by
initiating movement of the ultrasonic probe toward the subject using the articulated robot,
obtaining the reaction force acting on the ultrasonic probe when the ultrasonic probe contacts the body surface of the subject using the reaction force detection sensor, and
when the reaction force is greater than a predetermined value, stopping movement of the ultrasonic probe, obtaining the position of the ultrasonic probe using the position sensor, and setting and registering the position of the obtained ultrasonic probe as a body surface position of the subject,
moving the ultrasonic probe toward the subject,
determining a push-in amount of the ultrasonic probe with respect to the subject by comparing the position of the ultrasonic probe obtained using the position sensor and the set body surface position,
when the determined push-in amount of the ultrasonic probe is less than a reference push-in value, acquiring an ultrasonic image obtained from the ultrasonic diagnosis device during ultrasonic diagnosis, and recognizing a blood vessel in a body of the subject from the acquired ultrasonic image,
when the blood vessel is recognized, measuring a distance from the body surface of the subject to the blood vessel, and determining whether the measured distance has reached a predetermined effective depth of ultrasonic waves in a living body, and
stopping movement of the ultrasonic probe when the measured distance reaches the predetermined effective depth of ultrasonic waves in the living body; and
an output device configured to output a display or a warning of the push-in amount of the ultrasonic probe when the determined push-in amount of the ultrasonic probe is greater than the reference push-in value.

2. The ultrasonic diagnosis system according to claim 1, wherein the articulated robot includes an arm rotatable about a shaft via a motor, and the position sensor is an encoder that detects a rotational displacement amount of the motor.

3. An ultrasonic diagnosis system comprising:
an ultrasonic diagnosis device having an ultrasonic probe;
a moving device configured to move the ultrasonic probe;
a position sensor configured to detect a position of the ultrasonic probe; and
a control device configured to perform an ultrasonic diagnosis by
moving the ultrasonic probe toward the subject using the moving device,
determining a push-in amount of the ultrasonic probe with respect to the subject by based on a position of the ultrasonic probe obtained using the position sensor,
when the determined push-in amount of the ultrasonic probe is less than a reference push-in value, acquiring an ultrasonic image obtained from the ultrasonic diagnosis device during ultrasonic diagnosis, and recognizing a blood vessel in a body of the subject from the acquired ultrasonic image,
when the blood vessel is recognized, measuring a distance from the ultrasonic probe to the blood vessel, and determining whether the measured distance has reached an effective depth of ultrasonic waves in the body, and
stopping movement of the ultrasonic probe when the measured distance reaches the effective depth of ultrasonic waves in the body.

* * * * *